United States Patent [19]

Bauer et al.

[11] 4,329,503

[45] May 11, 1982

[54] PROCESS FOR THE PREPARATION OF 2-AMINO-4-NITROPHENOL

[75] Inventors: Wolfgang Bauer, Maintal; Klaus Kühlein, Kelkheim, both of Fed. Rep. of Germany

[73] Assignee: Cassella Aktiengesellschaft, Frankfurt am Main, Fed. Rep. of Germany

[21] Appl. No.: 226,120

[22] Filed: Jan. 19, 1981

[30] Foreign Application Priority Data

Jan. 23, 1980 [DE] Fed. Rep. of Germany ....... 3002254

[51] Int. Cl.$^3$ .................. C07C 89/00; C07C 85/11
[52] U.S. Cl. ................................. 564/418; 564/416; 564/419; 564/420
[58] Field of Search ............... 564/418, 416, 419, 420

[56] References Cited

U.S. PATENT DOCUMENTS 4,115,652 9/1978 Linhart et al. ...................... 568/706

FOREIGN PATENT DOCUMENTS 226217 3/1963 Austria ............................. 564/418
2140787 2/1973 Fed. Rep. of Germany ...... 564/418
5697 of 1898 United Kingdom ................ 564/418

Primary Examiner—John Doll
Attorney, Agent, or Firm—Connolly and Hutz

[57] ABSTRACT

The process of reducing 2,4-dinitrophenol to 2-amino-4-nitrophenol by reduction with a hydrosulfide in aqueous alkaline solution at temperatures from 20°–100° C. is improved by maintaining the pH at 7 to 9.5 during the reduction.

10 Claims, No Drawings

PROCESS FOR THE PREPARATION OF 2-AMINO-4-NITROPHENOL

The invention relates to a process for the preparation of 2-amino-4-nitrophenol by reduction of 2,4-dinitrophenol with hydrogen sulphide in aqueous alkaline solution at temperatures from 20° to 100° C.

It is known that 2-amino-4-nitrophenol can be prepared by partial reduction of 2,4-dinitrophenol. Electrolytic reduction (Ber.dtsch.chem.Ges. 41, 3196 (1908)) gives a yield of 13 to 53% of theory; reduction with sulphur dioxide in the presence of iron filings (German Pat. No. 289,454) gives a yield of 60% of theory; reduction with hydrazine in the presence of copper powder or iron powder (J.Pharm.Soc. Japan 76, 801 (1956), quoted in Chemical Abstracts 51, 1087 (1957)) in ethanolic solution gives a yield of 75% of theory. The above-mentioned processes give only inadequate yields of the desired product, or have other disadvantages, such as, for example, the use of large amounts of metal, the use of organic solvents or dangerous reactants, inadequate safety in operation or high pollution of the environment. Other known processes use, for the partial reduction of 2,4-dinitrophenol, sulphidic reducing agents, for example a mixture of ammonium sulphide and hydrogen sulphide (K. Auwers and H. Röhrig, Ber.dtsch.chem.Ges. 30, 988 (1897), yield: 32% of theory); disodium trisulphide (G.I. Gershzon, J.applied Chem. (USSR) 9, 879 (1936), compare Chem. Abstracts 30, 7554 (1936), yield: 70% of theory); disodium disulphide (P. E. Verkade et al Rec. trav. Chem. 65, 346 (1946) and British Patent Specification No. 594,816, yield: 59% of theory); and sodium sulphide (E. Marval and J. Urbik, Czechoslovak Pat. No. 90,290, compare Chem.Abstracts 54, P 24,552, yield: about 60% of theory, and Organic Synthesis, Col. Vol. III, yield: 64 to 67% of theory). Where the above-mentioned processes using sulphidic reducing agents give reasonable yields of the desired compound at all, isomeric 4-amino-2-nitrophenol is simultaneously undesirably formed and must be removed by separate purification operations. In some cases sulphur dyestuffs are also formed as undesired by-products and must be separated off in a manner which is troublesome and expensive with respect to equipment. Selective partial reduction of the nitro group in the 2-position of 2,4-dinitrophenol is said to be possible using alkali metal sulphides or polysulphides (U.S. Pat. No. 2,464,194) if the corresponding phenolate is reduced under very dilute conditions at 20° to 25° C. for 12 hours and then at about 80° C. The very dilute conditions required and the long reaction times make the process unprofitable.

In a more recent process (U.S. Pat. No. 4,115,652), 2,4-dinitrophenol is reduced in an aqueous ammoniacal solution containing, per mol of 2,4-dinitrophenol, 1 to 8 mols of ammonia and 2.5 to 6 mols of sodium hydrosulphide, at temperatures from room temperature to 100° C. The yields are 74 to 76% of theory. When this process was repeated, 5 to 10% of the undesired isomer were found in the resulting crude product, so that purification by the 2-amino-4-nitrophenolate must also be carried out with this process.

It has now been found, surprisingly, that a virtually selective, partial reduction of the nitro group in the 2-position of 2,4-dinitrophenol is possible with the aid of hydrosulphide in aqueous alkali solution at temperatures from 20° to 100° C. if the pH value does not exceed 9.5 during the reduction.

The hydrosulphides used in the process according to the invention can be those of the alkali metals (lithium, sodium, potassium, rubidium or caesium) or of the alkaline earth metals (for example calcium, strontium or barium), or that of ammonium. Sodium hydrosulphide, potassium hydrosulphide or ammonium hydrosulphide is preferably used. It is also possible to employ mixtures of two or more hydrosulphides. 3 to 4 mols of hydrosulphide are usually required per mol of 2,4-dinitrophenol.

The reduction is carried out in aqueous alkaline solution in a manner such that, according to the invention, the pH value does not exceed 9.5, preferably 9.0 and very particularly preferably 8.5, during the entire reduction. The pH value during the reduction is in the alkaline range between 7 and 9.5, preferably between 7.1 and 9.0 and very particularly preferably between 8.0 and 8.5. Free 2,4-dinitrophenol is dissolved in water, alkali metal hydroxide solution, for example sodium hydroxide solution or potassium hydroxide solution, being added in an amount such that a pH value of 7 to 9.5 is established. It is also advantageous for the starting material required to be produced in the reaction batch, for example by aqueous alkaline hydrolysis of 2,4-dinitrochlorobenzene. When the hydrolysis has ended, the pH value of the solution is measured and, if necessary, adjusted to 7 to 9.5. The hydrosulphide is metered in at a reaction temperature of 20° to 100° C., preferably 50° to 80° C., whilst monitoring the pH value of the reaction batch and appropriately whilst stirring. Throughout the entire period of the reduction, it is ensured that the pH value does not exceed 9.5, preferably 9.0 and very particularly preferably 8.5, by adding suitable substances which supply protons. An alkaline pH value maintained at a maximum of 9.5, preferably from 7.1 to 9.0 and very particularly preferably from 8.0 to 8.5, throughout the entire period of the reduction is thereby achieved. Suitable substances which supply protons are, for example, inorganic or organic acids, such as, for example, sulphuric acid, hydrochloric acid, phosphoric acid, carbonic acid, acetic acid, propionic acid, benzoic acid, benzenesulphonic acid, p-toluenesulphonic acid, amidosulphonic acid, carbamic acid or hydrogen sulphide; acid salts, such as, for example, sodium bisulphate or potassium bisulphate or ammonium bicarbonate; primary and secondary sodium phosphates, potassium phosphates and ammonium phosphates, or ammonium salts, such as, for example, ammonium chloride, ammonium sulphate or ammonium carbonate. In the case of buffer substances which supply protons, such as, for example, ammonium salts, it is also possible for the amount required to establish a pH value of 7 to 9.5 to be determined in a preliminary experiment and then for all of this amount to be added to the reaction batch before the start of the reduction. If buffer substances which supply protons are used, about 3 to 5 mols, in many cases about 3 to 4 mols, are required per mol of 2,4-dinitrophenol.

The use of hydrogen sulphide as the substance which supplies protons moreover provides the possibility of producing, in the reaction batch, the hydrosulphide required as the reducing agent. If hydrogen sulphide is used for producing the hydrosulphide in the reaction batch, it is expedient simultaneously to add alkaline compounds, such as alkali metal hydroxide, alkali metal carbonate or tertiary or secondary alkali metal phosphate, in order to obtain the pH values to be established in the process according to the invention. The alkali metal hydroxide, alkali metal carbonate or alkali metal phosphate thereby used is usually the sodium compound.

The process according to the invention is preferably carried out in water as the solvent. However, water-miscible solvents, for example from the series comprising monohydric or polyhydric alcohols, such as methanol, ethanol, isopropanol, glycol, glycol ethers, diethylene glycol and triethylene glycol, or water-immiscible solvents, for example methylene chloride, n-hexane, cyclohexane, toluene and monochlorobenzene, can also be added to the aqueous reaction medium. Furthermore, surface-active agents which are in themselves known, for example anionic surface-active agents, cationic surface-active agents or non-ionic surface-active agents (compare, for example, Ullmann's Enzyklopädie der Technischen Chemie (Ullmann's Encyclopedia of Industrial Chemistry), Volume 16, pages 724 to 748 (1965)) can be added to the reaction medium.

In the process according to the invention, selective partial reduction of the nitro group in the 2-position of 2,4-dinitrophenol can be carried out within short reaction times of down to about 30 minutes or even shorter. In the preferred temperature range of 50° to 80° C., as a rule reaction times of 45 minutes to 2 hours result. When the partial reduction has ended, the product is present in the reaction batch as the 2-amino-4-nitrophenolate and is usually separated off from the sulphur formed during the reduction. The following methods, for example, can be used for separating off the sulphur and isolating the 2-amino-4-nitrophenol.

1. When the partial reduction has ended, the 2-amino-4-nitrophenolate is isolated in the form of a sulphur-containing product by cooling and, if appropriate, by salting out by means of an electrolyte, such as sodium chloride, and is then dissolved again in a dilute strong acid, for example dilute hydrochloric acid, at pH values of 0 to 2. The sulphur is then filtered off and the 2-amino-4-nitrophenol is separated out in the filtrate by adjusting the pH value to 2 to 6, preferably 4.5 to 5.5. The product which has separated out is then isolated.

2. When the partial reduction has ended, the sulphur-containing reaction mixture is adjusted to a pH value of 2 to 6, preferably 4.5 to 5.5, with suitable acids, for example hydrochloric acid, and cooled and the 2-amino-4-nitrophenol which has separated out is isolated, together with the sulphur. The sulphur is then separated off, for example, as described in method 1, by converting the resulting 2-amino-4-nitrophenol into a solution of the readily water-soluble 2-amino-4-nitrophenol hydrochloride with aqueous hydrochloric acid and then filtering off the sulphur. 2-Amino-4-nitrophenol is separated out of the filtrate by adjusting the pH value to 2 to 6, preferably 4.5 to 5.5, and can then be isolated.

3. When the partial reduction has ended, in order to remove the sulphur, the sulphur-containing reduction mixture is (a) filtered in the alkaline range or (b) adjusted to pH values of 0 to 2 by adding a strong acid, preferably dilute hydrochloric acid, and then filtered. The pH value of the filtrate is adjusted to 2 to 6, preferably 4.5 to 5.5, by adding acids, such as, for example, hydrochloric acid, in case (a) and by alkaline substances, such as, for example, sodium hydroxide solution or sodium carbonate, in case (b), and the 2-amino-4-nitrophenol is thereby separated out and can then be isolated.

In the various working-up possibilities, it is expedient to remove small amounts of impurities, for example small amounts of sulphur, present in the alkaline, neutral or acid solutions by chemical reactions. For example, the sulphur can be converted into soluble thiosulphate by adding a sulphite, usually an alkali metal sulphite, preferably sodium sulphite, a pyrosulphite, usually an alkali metal pyrosulphite, in particular sodium pyrosulphite, or a bisulphite, usually an alkali metal bisulphite, preferably sodium bisulphite. Instead of adding a sulphite, it is also possible to pass sulphur dioxide into the alkaline solution. Besides sulphite, or sulphur dioxide, pyrosulphite or bisulphite, it is also possible to use a hydrosulphite (=dithionite, $S_2O_4^{2-}$), usually an alkali metal dithionite and preferably sodium dithionite.

Direct separating out and subsequent isolation of the 2-amino-4-nitrophenol by methods 2 and 3 described above by adjusting the pH value to 2 to 6, preferably 4.5 to 5.5, without the roundabout route via the 2-amino-4-nitro-phenolate is possible because virtually no by-products, such as isomeric 4-amino-2-nitrophenol or sulphur dyestuffs, are formed in the process according to the invention. (The separation method mentioned can also be advantageous in other cases in which virtually pure 2-amino-4-nitrophenol is present.) The process according to the invention gives 2-amino-4-nitrophenol in surprisingly high yields of 85 to 96% of theory and in outstanding purity. By suppressing the formation of sulphur dyestuffs and of undesired 4-amino-2-nitrophenol, which pollutes the effluent, an effluent which is ecologically more favourable is furthermore obtained in the process according to the invention.

The following examples serve to further illustrate the process according to the invention. Parts denote parts by weight and percentages denote percentages by weight; the temperatures are given in degrees centigrade. The melting points given are not corrected.

EXAMPLE 1

A suspension of 202.6 parts of 2,4-dinitrochlorobenzene in 300 parts of water and 7 parts of 32.6% strength sodium hydroxide solution is heated to about 90° C., and 256 parts of 32.6% strength sodium hydroxide solution are added at 90° to 95° C. in the course of about 3 hours, whilst stirring. The mixture is subsequently stirred at 90° to 95° C. for about 2 hours and 400 parts of water and 184 parts of ammonium chloride are added to the resulting 2,4-dinitrophenolate suspension, whereupon a pH value of 7.0 is established. 580 parts of a 31.9% strength hydrosulphide solution are then metered in at 70° to 75° C. in the course of about 45 minutes, whilst stirring continuously and continuously monitoring the pH value of the reduction batch, which rises to 8.6. The mixture is subsequently stirred at 70° to 75° C. for about 45 minutes. 40 parts of sodium chloride are then sprinkled in and the reaction mixture is then cooled to about 5° C. and filtered. 410 parts of a 39.6% strength aqueous press cake of sodium 2-amino-4-nitrophenolate, corresponding to 92% of the theoretical yield, are obtained. 410 parts of this press cake are introduced into 1,000 parts of water and are dissolved at pH ~1 with 225 parts of 30% strength aqueous hydrochloric acid. The sulphur is then filtered off and 116 parts of 32.6% strength sodium hydroxide solution are added to the aqueous solution of 2-amino-4-nitrophenol hydrochloride in order to establish a pH of 5. The yellow suspension of 2-amino-4-nitrophenol is subsequently stirred at 5° to 10° C. for about 1 hour and the product which has separated out is isolated by filtration. 324 parts of a 41.9% strength aqueous press cake of 2-amino-4-nitrophenol, corresponding to 135.8 parts of 100% pure 2-amino-4-nitrophenol (88% of theory, relative to 2,4-dinitrochlorobenzene) are obtained. A dried sample has a sulphur content of <0.1% and a melting point of 144° C.

EXAMPLE 2

202.6 parts of 2,4-dinitrochlorobenzene are converted into sodium 2,4-dinitrophenolate in accordance with the statements in Example 1 and, after adding 400 parts of water and 184 parts of ammonium chloride, the pH value is adjusted to 7.0. Reduction to sodium 2-amino-4-nitrophenolate is carried out with 580 parts of 31.9% strength hydrosulphide solution at pH values of at most 9, whilst stirring and monitoring the pH. After addition of the hydrosulphide, the mixture is subsequently stirred at 70° to 75° C. for about 45 minutes and the sulphur which has precipitated is filtered off. 100 g of sodium sulphite are added to the filtrate and the mixture is cooled to about 15° C. and adjusted to a pH of 5.6 to 5.8 with 136 parts of 30% strength hydrochloric acid. The mixture is subsequently stirred for about a further hour at 5° to 10° C. and filtered and the filter cake is rinsed with about 200 parts of 26% strength aqueous sodium chloride solution. 277.6 parts of a 53.3% strength aqueous press cake of 2-amino-4-nitrophenol, corresponding to 147.9 parts of 100% pure 2-amino-4-nitrophenol (96% of theory, relative to 2,4-dinitrochlorobenzene) are obtained. The product has a sulphur content of <0.1% and a melting point of 144° C.

EXAMPLE 3

Sodium 2,4-dinitrophenolate is prepared from 202.6 parts of 2,4-dinitrochlorobenzene in accordance with the statements of Example 1. The hydrosulphide reduction of the 2,4-dinitrophenolate suspension, to which 400 parts of water and 184 parts of ammonium chloride have been added, is then carried out in accordance with the statements of Example 1. After the reduction, the sulphur-containing reaction mixture is adjusted to pH 7 with 216 parts of 30% strength hydrochloric acid and the mixture is subsequently stirred at 40° to 45° C. for about 1 hour in order to complete precipitation of the sulphur. The pH is then adjusted to 9 with 135 parts of 32.6% strength aqueous sodium hydroxide solution and the sulphur is filtered off. 43.6 parts of sodium sulphite are first added to the red filtrate of sodium 2-amino-4-nitrophenolate, and the mixture is then adjusted to pH 5.6 with 158 parts of 30% strength hydrochloric acid. The aqueous 2-amino-4-nitrophenol suspension is subsequently stirred at 5° to 10° C. for about 1 hour and the product is isolated by filtration.

228 parts of a 62.3% strength aqueous press cake of 2-amino-4-nitrophenol, corresponding to 142 parts of 100% pure 2-amino-4-nitrophenol (92% of theory; relative to 2,4-dinitrochlorobenzene) are obtained; sulphur content: <0.1%, melting point: 143° to 144° C.

EXAMPLE 4

The procedure followed is as according to the statements of Example 3, but no ammonium chloride is added and instead the pH value is kept in the range from 8 to 9.2 during the reduction by continuously adding a total of 330 parts of 50% strength acetic acid.

230.5 parts of a 59.5% strength aqueous paste of 2-amino-4-nitrophenol, corresponding to 137.1 parts of 100% pure 2-amino-4-nitrophenol (89% of theory, relative to 2,4-dinitrochlorobenzene) are obtained.

EXAMPLE 5

The procedure followed is as according to the statements of Example 3, but no ammonium chloride is added and instead the pH value is kept in the range from 8 to 9.0 during the reduction by continuous portionwise addition of a total of 200 parts of sodium dihydrogen phosphate. 720 parts of a 19.3% strength aqueous press cake of 2-amino-4-nitrophenol, corresponding to 139 parts of 100% pure 2-amino-4-nitrophenol, are obtained. Yield: 90% of theory, relative to the 2,4-dinitrochlorobenzene employed.

EXAMPLE 6

A suspension of 184.1 parts of 2,4-dinitrophenol in 250 parts of water is heated to 70° C., and 127 parts of 30.2% strength aqueous sodium hydroxide solution are added. The pH value is then adjusted to 7.0 by adding 35.6 parts of ammonium chloride. 580 parts of a 31.9% strength aqueous hydrosulphide solution are then added in the course of about 45 minutes, whilst stirring and monitoring the pH value, and a total of a further 197 parts of ammonium chloride is introduced in portions during the addition of the hydrosulphide solution. A pH value of 8.6 is thereby not exceeded throughout the entire period of the reduction. The mixture is subsequently stirred for about a further 45 minutes and cooled to 20° to 25° C. and 35 parts of sodium sulphite are sprinkled in. Thereafter, the pH value of the reduction mixture is adjusted to 5 by slowly adding 244 parts of 30% strength hydrochloric acid and the mixture is subsequently stirred at 5° to 10° C. for about 1½ hours. It is then filtered and the sulphur-containing press cake of 2-amino-4-nitrophenol is washed with 100 parts of 26% strength sodium chloride solution.

The press cake is then introduced into 400 parts of water, and 53 parts of sodium carbonate are added. The mixture is then heated to 50° to 55° C. and the sulphur is removed by filtration. The filtrate is adjusted to pH 5 with about 98 parts of 30% strength hydrochloric acid, and the 2-amino-4-nitrophenol suspension is subsequently stirred at about 5° C. for about 2 hours. After the filtration, 346 parts of a 41% strength aqueous filter cake of 2-amino-4-nitrophenol, corresponding to 141.9 parts of 100% pure 2-amino-4-nitrophenol, are obtained. Yield: 92% of theory, relative to 2,4-dinitrophenol.

EXAMPLE 7

Sodium 2,4-dinitrophenolate is prepared from 202.6 parts of 2,4-dinitrochlorobenzene in accordance with the statements of Example 1. 92 parts of ammonium chloride are added to the suspension of the 2,4-dinitrophenolate at 70° C., a pH value of 7.1 being established. 290.4 parts of 31.9% strength aqueous hydrosulphide solution are then added in the course of about 20 minutes, whilst stirring and monitoring the pH value. The pH value is reduced from 8.4 to 8.0 by adding a further 92 parts of ammonium chloride, and a further 290.4 parts of 31.9% strength hydrosulphide solution are then added at 70° to 75° C. in the course of about 20 minutes. The pH value thereby rises to 8.4. The reaction mixture is then subsequently stirred at about 70° C. for about 45 minutes. It is cooled to 15° to 20° C., 35 parts of sodium sulphite are added, followed by about 230 parts of 30% strength aqueous hydrochloric acid, in order to adjust the pH to 5. The sulphur-containing 2-amino-4-nitrophenol suspension is subsequently stirred at 5° to 10° C. for about 1½ hours and is then filtered. 438.4 parts of a 34% strength aqueous paste of 2-amino-4-nitrophenol with a sulphur content of about 19% are obtained. This sulphur-containing filter cake is introduced into a solution of 53 parts of sodium carbonate in 400 parts of water. The mixture is warmed to about 55° to 60° C. and the sulphur is removed from the solution of sodium 2-amino-4-nitrophenolate by filtration. The filtrate is then cooled to about 20° C. and adjusted to pH 5 with about 107 parts of 30% strength aqueous hydrochloric acid. After cooling the mixture to about 5° C., it is filtered. 344 parts of a 42.1% strength aqueous press cake of 2-amino-4-nitrophenol, corresponding to 144.8 parts of 100% pure 2-amino-4-nitrophenol, are obtained. Yield: 94% of theory, relative to 2,4-dinitrochlorobenzene.

EXAMPLE 8

Sodium 2,4-dinitrophenolate is prepared from 202.6 parts of 2,4-dinitrochlorobenzene in accordance with the statements of Example 1. The suspension of the 2,4-dinitrophenolate is adjusted to pH 7.5 with 30% strength aqueous hydrochloric acid. 580 parts of a 31.4% strength hydrosulphide solution and at the same time 259 parts of 30% strength aqueous hydrochloric acid are then metered in at 70° to 75° C. in the course of about 1 hour, during which a pH value of 8.5 is not exceeded. When the reduction has ended, the sulphur is filtered off. 70 parts of sodium sulphite (or alternatively: 52.3 parts of sodium pyrosulphite or 57.2 parts of sodium bisulphite) are added to the sodium 2-amino-4-nitrophenolate solution and the mixture is then adjusted to pH 3.8 with 30% strength hydrochloric acid. The 2-amino-4-nitrophenol suspension is then cooled to 0° to 5° C. and the product is isolated by filtration. Yield: 202 g of 71.5% strength 2-amino-4-nitrophenol, corresponding to 144.4 g of 100% pure 2-amino-4-nitrophenol (93% of theory, relative to 2,4-dinitrochlorobenzene).

A dried sample has a melting point of 144° C.

If, instead of adding sodium sulphite, sodium pyrosulphite or sodium bisulphite after filtering off the sulphur, sulphur dioxide is passed into the weakly alkaline 2-amino-4-nitrophenolate solution until the pH value is 4.5, 2-amino-4-nitrophenol is likewise obtained in a yield of 93% of theory.

EXAMPLE 9

The preparation of sodium 2,4-dinitrophenolate and the hydrosulphide reduction to give sodium 2-amino-4-nitrophenolate is carried out in accordance with the statements of Example 8. When the reduction has ended, the sulphur-containing 2-amino-4-nitrophenolate solution is added to 310 parts of 30% strength aqueous hydrochloric acid. The sulphur is filtered off from the solution of 2-amino-4-nitro-phenol hydrochloride and 8 parts of concentrated hydrosulphite (sodium dithionite) are added to the filtrate. A pH value of 3.9 is then established with 30% strength sodium hydroxide solution and the 2-amino-4-nitrophenol suspension is cooled to 0°–5° C. After filtration, 190 g of 74.8% strength 2-amino-4-nitrophenol, corresponding to 142.1 g of 100% pure 2-amino-4-nitrophenol (92% of theory, relative to 2,4-dinitrochlorobenzene) are obtained.

EXAMPLE 10

Sodium 2,4-dinitrophenolate is prepared from 202.6 parts of 2,4-dinitrochlorobenzene in accordance with the statements of Example 1. 150 parts of water are then added and the mixture is cooled to 65° to 70° C. and adjusted to pH 8 with 8 parts of 30% strength hydrochloric acid.

102 g of hydrogen sulphide and at the same time 30 parts of 30% strength sodium hydroxide solution are then metered in under normal pressure in the course of about 3 hours (or alternatively in a pressure vessel under a maximum of 5 bars in the course of 1 hour) at 65° to 70° C., whereupon a pH value of 8 to 8.5 is established.

After the addition of the hydrogen sulphide, the mixture is subsequently stirred for about a further 15 minutes at 65° to 70° C. The sulphur-containing 2-amino-4-nitrophenolate solution is then added to 310 parts of 30% strength hydrochloric acid.

The solution of 2-amino-4-nitrophenol hydrochloride is filtered at 60° to 70° C. and the filtrate is mixed with a solution of 25 g of sodium sulphite in 240 parts of 30% strength sodium hydroxide solution. A pH value of 3.6 to 4 is then established, the 2-amino-4-nitrophenol suspension is cooled to 0° to 5° C. and filtered and the material on the filter is rinsed with a little ice-water.

Yield: 176.5 g of 74.8% strength 2-amino-4-nitrophenol, corresponding to 132 g of 100% pure 2-amino-4-nitrophenol (86% of theory, relative to 2,4-dinitrochlorobenzene).

The hydrosulphide solution used in the above examples is an aqueous solution of sodium hydrosulphide. The 2-amino-4-nitrophenol is used, for example, as an intermediate product for the preparation of metal complex dyestuffs.

What is claimed is:

1. In the process for preparation of 2-amino-4-nitrophenol by reduction of 2,4-dinitrophenol with a hydrosulfide in aqueous alkaline solution at temperatures from 20° to 100° C., the improvement comprises maintaining the pH value at 7 to 9.5 during the reduction.

2. The process according to claim 1 wherein the pH value does not exceed 8.5 during the reduction.

3. The process according to claim 1 wherein a pH value of 8.0 to 8.5 is maintained during the reduction.

4. The process according to claim 1 wherein the reduction is carried out at a temperature of 50° to 80° C.

5. The process according to claim 1 wherein 3 to 4 mols of a hydrosulfide of an alkali metal, alkaline earth metal, or ammonium are used for the reduction of each mol of 2,4-dinitrophenol.

6. The process according to claim 1 wherein the pH value is maintained by portionwise or continuous addition of substances which supply protons.

7. The process according to claim 1 wherein the pH value is maintained by adding a buffer substance before the start of the reduction.

8. The process according to claim 1 wherein at the end of the reduction any sulphur present in the reaction mixture is removed by filtration, the pH value of the filtrate is adjusted to 2 to 6 and product 2-amino-4-nitrophenol is separated.

9. The process according to claim 1 wherein at the end of the reduction any sulphur present in the reaction mixture is removed by filtration, after the filtration impurities still present in the filtrate are removed by chemical reaction with an alkali metal sulphite, sulphur dioxide, alkali metal pyrosulphite, alkali metal bisulphite or alkali metal dithionite, and then the pH value of the filtrate is adjusted to 2 to 6 whereby product 2-amino-4-nitrophenol is separated.

10. The process according to claim 1 wherein the hydrosulfide is sodium hydrosulfide.

* * * * *